United States Patent
Van Tunen

(10) Patent No.: US 9,714,432 B2
(45) Date of Patent: *Jul. 25, 2017

(54) USE OF JAZ5A FOR IMPROVING DROUGHT-RESISTANCE IN A PLANT

(75) Inventor: Adrianus Johannes Van Tunen, Wageningen (NL)

(73) Assignee: Keygene N.V., Wageningen (NL)

( * ) Notice: Subject to any disclaimer, the term of this patent is extended or adjusted under 35 U.S.C. 154(b) by 188 days.

This patent is subject to a terminal disclaimer.

(21) Appl. No.: 14/131,184

(22) PCT Filed: Jul. 5, 2012

(86) PCT No.: PCT/NL2012/050481
§ 371 (c)(1),
(2), (4) Date: Mar. 24, 2014

(87) PCT Pub. No.: WO2013/006058
PCT Pub. Date: Jan. 10, 2013

(65) Prior Publication Data
US 2014/0223596 A1   Aug. 7, 2014

Related U.S. Application Data

(60) Provisional application No. 61/505,391, filed on Jul. 7, 2011.

(51) Int. Cl.
*A01H 5/00* (2006.01)
*C12N 15/82* (2006.01)
*C12N 15/29* (2006.01)
*C07K 14/415* (2006.01)
*C12Q 1/68* (2006.01)

(52) U.S. Cl.
CPC ........ *C12N 15/8273* (2013.01); *C07K 14/415* (2013.01); *C12Q 1/6895* (2013.01)

(58) Field of Classification Search
None
See application file for complete search history.

(56) References Cited

U.S. PATENT DOCUMENTS

| | | | | |
|---|---|---|---|---|
| 6,515,202 B1 * | 2/2003 | Crane | .................... | C12N 9/001 435/189 |
| 7,482,510 B2 * | 1/2009 | da Costa e Silva | . | C07K 14/415 435/320.1 |
| 9,284,572 B2 * | 3/2016 | He | ........................ | C07K 14/415 |
| 2006/0107345 A1 | 5/2006 | Alexandrov et al. | | |
| 2009/0158466 A1* | 6/2009 | Wan | ................... | C12N 15/8273 800/289 |
| 2010/0037352 A1* | 2/2010 | Alexandrov | ........ | C07K 14/415 800/298 |
| 2013/0167266 A1 | 6/2013 | He et al. | | |

FOREIGN PATENT DOCUMENTS

| | | |
|---|---|---|
| CN | 101585870 | 11/2009 |
| CN | 101585871 | 11/2009 |
| CN | 101638658 | 2/2010 |
| WO | WO-99/04013 A2 | 1/1999 |
| WO | WO-2004/020642 | 3/2004 |
| WO | WO-2006/055631 A2 | 5/2006 |
| WO | WO-2012/005591 | 1/2012 |

OTHER PUBLICATIONS

Friedberg (Brief. Bioinformatics (2006) 7: 225-242).*
Lacombe et al (Science (2001) vol. 292, pp. 1486-1487).*
Kwon et al (GenBank Accession No. AC172887 available online Sep. 16, 2008)—Alignment data presented in Office Action.*
Gelvin (Microbiology and Molecular Biology Reviews, Mar. 2003, p. 16-37).*
Chini et al (Nature 448, (Aug. 9, 2007) 666-671).*
Database Geneseq [Online] Mar. 1, 2012, "*Brassica rapa* subsp. *chinensis* BccJAZ5a protein sequence, SEQ:2", Database Assession No. XP 002684038.
Database Geneseq [Online] Mar. 1, 2012, "*Brassica rapa* subsp. *chinensis* BccJAZ5a protein sequence, SEQ:4", Database Assession No. XP 002684037.
Database Geneseq [Online] Sep. 30, 2010, "Plant isolated polypeptide sequence, SEQ ID 825,", Database Assession No. XP 002684035.
Search Report received in International Application No. PCT/NL2012/050481 mailed Oct. 9, 2012,
Seo, Yean Joo et al.,"Overexpression of the Ethylene-Responsive Factor Gene CrERF4 from Brassica rapa Increases Tolerance to Salt and Drought in Arabidopsis Plants,", Molecules and Cells, vol. 30, No. 3, Sep. 2010, pp. 271-277.
Altschul, et al. "Basic Local Alignment Search Tool", J. Mol. Biol, 1990, vol. 215, pp. 403-410.
Devereux, et al. "A Comprehensive set of sequence analysis programs for the VAX", Nucleic Acids Research, 1984, vol. 12, No. 1, pp. 387-395.
Guo et al., "Protein tolerance to random amino acid change", PNAS, Jun. 22, 2004, vol. 101, No. 25, pp. 9205-9210.
International Search Report issued in International Patent Application No. PCT/NL2011/050499, dated Sep. 19, 2011.
Kaur, et al., "Genetic map construction and QTI mapping of resistance to blackleg (*Leptosphaeria maculans*) disease in Australian canola (*Brassica napus* L.) cultivars", Theoretical and Applied Genetics, vol. 120, No. 1, 2009, pp. 71-83.

(Continued)

*Primary Examiner* — Lee A Visone
(74) *Attorney, Agent, or Firm* — Sunit Talapatra; Tianran Yan; Foley & Lardner LLP

(57) ABSTRACT

The present invention provides use of a plant gene JAZ5a for improving drought-resistance of a plant. It further provides a method for improving the drought-resistance of a plant, comprising enhancing the expression or activity of Jaz5A in said plant.

10 Claims, 2 Drawing Sheets

(56) References Cited

OTHER PUBLICATIONS

Sequence Alignment of SEQ ID No. 2—Generated on Jul. 30, 2015.
Wang, et al. "Plant responses to drought, salinity and extreme temperatures: towards genetic engineering for stress tolerance", Planta, 2003, vol. 218, pp. 1-14.

* cited by examiner

SEQUENCE LISTING

```
<160> NUMBER OF SEQ ID NOS: 6

<210> SEQ ID NO 1
<211> LENGTH: 1587
<212> TYPE: DNA
<213> ORGANISM: Brassica campestris L. ssp. chinensis

<400> SEQUENCE: 1
ataaaacaca tgagcgagct cgacgcatcc cacttctctt tcttccattt gacgcacaga      60
aaaaggaaaa ataagataac aaatacataa ctaaaaacaa acagaattct ggagaatctc     120
tccttattat tcacaatatg tcaagaaatg aagatggtga ggcaccaccg ccggagaagt     180
ccaacttcac ccggcgatgt agtttgctca gccgttactt gaaggagaag ggtagtttcg     240
gtaatataga tcttggattg gtccgaaagc ctggtccgga tctcgggtta cccggaaact     300
ctgatcaaca aggtacttta tatcttccta gctctcacgt ccgccacttg taatagtaaa     360
gtctggtttt attttattta tttgcaagtc acttccttaa aactcgaatt aatctacttt     420
tgtaatatgt aaccaggaaa atataagaag agaatttagt tgattttgga aactgatacg     480
gttcatgaat cgcaaaaaat aattattttt tgtagagttt attcgtttga tgattccaat     540
aaagcttata agagtttttt attctcttta ttcagagaaa caaaatgtga tgcataaggc     600
aaattcggaa ctcaaagccc ttaatgtctt aggcgaaccc tctagttcat ttggaggcaa     660
agccaaagct accaatctca ggtgagatct ataataatac ttgttgctct tccggtttta     720
aatggttctc ttctgaaacc ggattttggt ttacagtgaa ccatcagagc caattagttc     780
tcagctgaca atattctttg gaggaaaagt tctagtatac aatgagtttc cttcagacaa     840
agctaaagag ataatacagg tagcaaaaga agccaagtct gtgactgata ttaacattca     900
gacacaaatc aatgtccaaa aggaccacaa caaaagcaac atagttcttc ctgatctcaa     960
cgagcccaca gatactgcgg atgtcaatca acagcaacaa caacaaaacc agctcgtgga    1020
acgtatagca cgtagagctt ccttacatcg cttctttgct aaacgtaaag acaggtaaac    1080
atagcttgac tagttcaaaa gattatgtat ttgaaaacta taagtgctct taaatgatcc    1140
tagtaatcaa tcaaaaccgc gatagatact cacatgacaa ttttcgtata ttttgttttt    1200
tcatcacagg gctgtggcta gagctccata ccaagttaac caaaatggtg gtggtcatca    1260
ttatcctccg aagccagaga ctgtacctgg tcaacagcta gagcagggac agtcgtcaca    1320
accacaacga ccggctcaac ccaaaccaga atgtgataaa gatatgttga tggaagttaa    1380
ggaagaaggc cagtgttcga aagatctcga acttaggcta taatcaaatt ttgttaaata    1440
tttgtaagaa acttaaactt aagatgatcg tctgacttat tttaaatgat ttttgctttg    1500
tactaaagtt tgcaaccaat ttttaacttg gatattaata aatgcaatag tgaatttagt    1560
tgcaatttat aacaatttga tttgcaa                                        1587
```

<210> SEQ ID NO 2
<211> LENGTH: 813
<212> TYPE: DNA
<213> ORGANISM: Brassica campestris L. ssp. chinensis

<400> SEQUENCE: 2

| | | | | | |
|---|---|---|---|---|---|
| atgtcaagaa | atgaagatgg | tgaggcacca | ccgccggaga | agtccaactt | cacccggcga | 60 |
| tgtagtttgc | tcagccgtta | cttgaaggag | aagggtagtt | tcggtaatat | agatcttgga | 120 |
| ttggtccgaa | agcctggtcc | ggatctcggg | ttacccggaa | actctgatca | acaagagaaa | 180 |
| caaaatgtga | tgcataaggc | aaattcggaa | ctcaaagccg | ttaatgtctt | aggcgaaccc | 240 |
| tctagttcat | ttggaggcaa | agccaaagct | accaatctca | gtgaaccatc | agagccaatt | 300 |
| agttctcagc | tgacaatatt | ctttggagga | aaagttctag | tatacaatga | gtttccttca | 360 |
| gacaaagcta | aagagataat | acaggtagca | aaagaagcca | agtctgtgac | tgatattaac | 420 |
| attcagacac | aaatcaatgt | ccaaaaggac | acaacaaaaa | gcaacatagt | tcttcctgat | 480 |
| ctcaacgagc | ccacagatac | tgcggatgtc | aatcaacagc | aacaacaaca | aaaccagctc | 540 |
| gtggaacgta | tagcacgtag | agcttcctta | catcgcttct | ttgctaaacg | taaagacagg | 600 |
| gctgtggcta | gagctccata | ccaagttaac | caaaatggtg | gtggtcatca | ttatcctccg | 660 |
| aagccagaga | ctgtacctgg | tcaacagcta | gagcagggac | agtcgtcaca | accacaacga | 720 |
| ccggctcaac | ccaaaccaga | atgtgataaa | gatatgttga | tggaagttaa | ggaagaaggc | 780 |
| cagtgttcga | agatctcga | acttaggcta | taa | | | 813 |

<210> SEQ ID NO 3
<211> LENGTH: 1825
<212> TYPE: DNA
<213> ORGANISM: Brassica campestris L. ssp. chinensis

<400> SEQUENCE: 3

| | | | | | |
|---|---|---|---|---|---|
| gaggcttaca | ggttcaacca | tttcagtaga | accttccaac | atctggaaac | gatcaaagga | 60 |
| gcaactcttt | gacagccgta | cgatcaaaac | tcatttgaca | catctcagtt | tctcactgac | 120 |
| ttcctctcag | tcatcagctt | tctccttctc | tttcttcaga | tctctgcttc | ttctcctcgg | 180 |
| tttcaatgtc | gctccatctt | cttctccttc | ttctgctact | atcccttgga | gcaccttctt | 240 |
| tgctccaagc | gtcggtgcat | gagtaccgta | gcgagagatt | catgtccaaa | ggcaacgcct | 300 |
| ttgtcttcca | cggcggcagt | gaaggcatct | actcctcttc | tccctccgac | aacttctcct | 360 |
| ccgactctga | ttccctctcc | tcctttatcc | ggtaaagttc | tatgattccg | tttctttaac | 420 |
| taaagtttcc | tcttttaaat | ctgcttagga | tctgactttg | taatcagaac | ccattaggat | 480 |
| tcttcgtcta | cgagttggat | cttagagctg | attaagttcg | tttgtataca | gttcttagct | 540 |
| gtttctcggt | gaaagtttct | tactttgaaa | ctctgtgtgt | gtcctctctg | agtaagcatt | 600 |
| gcttccacgt | gtcaaagatt | tgaactttca | ttgtgttttg | agtaaaatct | tagctgtttc | 660 |
| tctgtaaaag | tttctaactt | tgaaactctg | tttgtatcct | ctctgagtaa | acatttcttc | 720 |
| cacgtgtcaa | aagagctgaa | cttttcctcgt | gtttgagtaa | catcttagct | gtttctctgt | 780 |
| gaaagcttct | tactttgaaa | ctctgtgtgt | gtcctctctg | agtaaacatt | gcttccacgt | 840 |
| gtcaaagagt | tgaactttcc | ttgtgtttga | gtaacatctt | agctgtttct | ctgtgaaagt | 900 |
| tcttacttg | ctaatgcatt | taacagtttt | gagaagatca | cattccggag | acccgaggaa | 960 |
| gcttccaaca | cctcttcatt | acctatccac | gccgtccttt | tcgaggtaga | agacagggag | 1020 |

```
aacatcggag gatcagctta cggtgggcag agagctgtct gctgcacatc tgatctcgcc      1080
aaactcggtg tttgctcaca cggagagatc atccaccatc cttcttctaa agactcctcc      1140
tggcctcaag tcttcggtgt tcctttgtt  gagaatgatt tgtctgctac gctgcttaca      1200
agatcgattc agatcactag gacaggaatg tataacctct acttcatcca ctgtgatcct      1260
gctctcaagg acttggtcgt tgaaggcaaa accatctgga aaaccctgg  aggatactta      1320 ccaggtagaa tggctccgtt gatgtacttc tacgggttca tgtctctcgc ctttgtgctc      1380
ctcggagtct tctggttctc ccagtgcgct aggttctgga gagaagtgct tcccttgcag      1440
aactgtgtaa ctttagtgat aacgcttggg atgtgcgaga tggcgctttg gtacttcgac      1500
tacgctgagt caacgagac  tggtgttaga ccaacggtga tcaccgtatg ggcagtcacg      1560
tttgggtgta tcaaacgcac gtgcgcacgt gtcatcatcc ttatggtttc gatggggtac      1620
ggtgtcgtga ggcctacgct tggtgggttt acatcgaagg tgatcatgct tggtgtcact      1680
ttcttcgctg cttccgagac tcttgagctg ttggagaatg ttggtgcggt tagtgacttc      1740
tcagggaaag cgagactgtt tttggttctc cccgttgcgg tgttggatgc tttcttcatc      1800
atatggatat tcaagtcgct ttcgg                                            1825
```

<210> SEQ ID NO 4
<211> LENGTH: 270
<212> TYPE: PRT
<213> ORGANISM: Brassica campestris L. ssp. chinensis

<400> SEQUENCE: 4

```
Met Ser Arg Asn Glu Asp Gly Glu Ala Pro Pro Glu Lys Ser Asn
1               5                   10                  15

Phe Thr Arg Arg Cys Ser Leu Leu Ser Arg Tyr Leu Lys Glu Lys Gly
            20                  25                  30

Ser Phe Gly Asn Ile Asp Leu Gly Leu Val Arg Lys Pro Gly Pro Asp
            35                  40                  45

Leu Gly Leu Pro Gly Asn Ser Asp Gln Gln Lys Gln Asn Val Met
    50                  55                  60

His Lys Ala Asn Ser Glu Leu Lys Ala Val Asn Val Leu Gly Glu Pro
65                  70                  75                  80

Ser Ser Ser Phe Gly Gly Lys Ala Lys Ala Thr Asn Leu Ser Glu Pro
                85                  90                  95

Ser Glu Pro Ile Ser Ser Gln Leu Thr Ile Phe Gly Gly Lys Val
            100                 105                 110

Leu Val Tyr Asn Glu Phe Pro Ser Asp Lys Ala Lys Glu Ile Ile Gln
            115                 120                 125

Val Ala Lys Glu Ala Lys Ser Val Thr Asp Ile Asn Ile Gln Thr Gln
        130                 135                 140

Ile Asn Val Gln Lys Asp His Asn Lys Ser Asn Ile Val Leu Pro Asp
145                 150                 155                 160

Leu Asn Glu Pro Thr Asp Thr Ala Asp Val Gln Gln Gln Gln
                165                 170                 175

Gln Asn Gln Leu Val Glu Arg Ile Ala Arg Arg Ala Ser Leu His Arg
            180                 185                 190

Phe Phe Ala Lys Arg Lys Asp Arg Ala Val Ala Arg Ala Pro Tyr Gln
            195                 200                 205

Val Asn Gln Asn Gly Gly Gly His His Tyr Pro Pro Lys Pro Glu Thr
        210                 215                 220

Val Pro Gly Gln Gln Leu Glu Gln Gly Gln Ser Ser Gln Pro Gln Arg
```

```
                    225                 230                 235                 240
Pro Ala Gln Pro Lys Pro Glu Cys Asp Lys Asp Met Leu Met Glu Val
                245                 250                 255

Lys Glu Glu Gly Gln Cys Ser Lys Asp Leu Glu Leu Arg Leu
                260                 265                 270

<210> SEQ ID NO 5
<211> LENGTH: 18
<212> TYPE: DNA
<213> ORGANISM: Artificial sequence
<220> FEATURE:
<223> OTHER INFORMATION: forward primer

<400> SEQUENCE: 5
aagaagccaa gtctgtga                                                 18

<210> SEQ ID NO 6
<211> LENGTH: 18
<212> TYPE: DNA
<213> ORGANISM: Artificial sequence
<220> FEATURE:
<223> OTHER INFORMATION: reverse primer

<400> SEQUENCE: 6
tcggaggata atgatgac                                                 18
```

USE OF JAZ5A FOR IMPROVING DROUGHT-RESISTANCE IN A PLANT

TECHNICAL FIELD

The present invention belongs to the fields of biotechnology and botany. The present invention relates to a new method for improving drought resistance of a plant. The invention involves the use of a protein in said plant for improving drought resistance. The present invention relates to the enhancement of the expression or activity of the protein, thereby providing improved drought resistance to a plant in comparison to a plant not modified to enhance expression of the protein.

BACKGROUND ART

Cabbages mainly include *Brassica campestris* L. ssp. *Pekinensis* and *Brassica campestris* L. ssp. *chinensis*. *Brassica campestris* L. ssp. *chinensis* is also named as green cabbage, and baby *Brassica campestris* L. ssp. *chinensis* in the north of China. *Brassica campestris* L. ssp. *chinensis* exhibits high adaptability, growth, productivity and nutrition. It is the most consumed vegetable among various vegetables and widely grew in the provinces in the regions of Changjiang valley in China. There are various types and varieties of *Brassica campestris* L. ssp. *chinensis*. Cabbages have a short growth period, wide adaptability, and high productivity. They are also easy to plant, which allows for a sustained perennial supply.

The products of *Brassica campestris* L. ssp. *chinensis* are fresh and tender, have rich nutrition and win favor of consumers. *Brassica campestris* L. ssp. *chinensis* comprises about 30-40% of the total domestic vegetable productivity a year, and also makes a significant contribution in supplementing vegetables in slack seasons and balancing the vegetable supply over a whole year. Both the *Brassica campestris* L. ssp. *Pekinensis* and *Brassica campestris* L. ssp. *chinensis* favor cool weather and can be planted perennially. The most suitable growth temperature is 15-20° C. In recent years, to meet the market demand, cabbages are mainly planted by the technique of intensive culture. To ensure an even production and supply among the four seasons, *Brassica campestris* L. ssp. *chinensis* generally needs to be planted in different manners in different seasons. In the past, *Brassica campestris* L. ssp. *chinensis* was mainly planted in spring and winter. Now people begin to plant *Brassica campestris* L. ssp. *chinensis* in torrid summer and autumn by various culture manners. This will undoubtedly make *Brassica campestris* L. ssp. *chinensis* subject to the stress from drought during its growth, especially in late spring, summer and early autumn.

The *Brassica campestris* L. ssp. *chinensis* cultured in the seasons of high temperature can go to the market in bulk after a 20-day culture. However, the high temperatures usually lead to an elongated internode, slowed growth, bitter taste and undesirably increased fiber, etc. This will result in low productivity and poor quality. As a result, the price rises and the supply falls short of demand. The consumer demand cannot be met. *Brassica campestris* L. ssp. *Pekinensis* has poor tolerance to drought. It is highly drought sensitive in the rosette stage and the heading stage. If the average temperature is too high, the heart leaf can not amplexate to build a tight bulb, or can not bulb up at all. Even if it constrainedly bulbs up, the heading is loose. In the natural field conditions in summer, the production relies on the drought-resistance plants' capability of forming a normal leafy head. And the capability of heading formation under the natural high temperature in fields becomes an indication of a drought-resistance in *Brassica campestris* L. ssp. *Pekinensis*.

Both the *Brassica campestris* L. ssp. *Pekinensis* and the *Brassica campestris* L. ssp. chinensis were originally planted in China. In foreign countries, there is few studies on breeding of cabbages. Varieties of Japanese, Korean and Formosan origins are poor in drought resistance, and unsuitable for planting in China. Domestically dominant are mainly the disease resistant varieties planted in autumn. Vegetables of cabbages have a narrow gene library for drought-resistance. Breeding of drought-resistance cabbage variety is limited to the screening among the cabbage materials, whereby only some varieties with poor drought resistance and low stress resistance have been obtained.

To solve these problems, the domestic breeding experts have utilized the traditional breeding methods to widely screen and culture drought-resistance varieties of vegetables of cabbages, to introduce drought-resistance genes, and broaden the sources of exploitation, which improved the drought-resistant ability of vegetables of cabbages to a certain degree and have produced effect in actual production. However, the current methods are limited to the assessment of drought resistance under the local climate and the morphological changes under a high temperature stress. These methods are not suitable for the temperate areas, which can not provide the field conditions with suitable selection stresses. Even if a single drought-resistance plant was selected, a series of complicated methods and means would be required to maintain the drought-resistance in the seeds collected until the next spring. The screening requires a long period, and is geographically limited, which can not provide a drought resistant variety universally adaptable. Therefore, it is an urgent task in breeding of drought-resistance vegetables of cabbages to intensively study the occurrence and development of the drought damages during the seedling stage, and to develop a method and technique for screening drought resistance in seedling stage, which provides improved operability, stability, efficiency and adaptability. The traits closely associated with the drought resistance in cabbages are of a quantitative nature, which poses great difficulties in genotyping. Particularly for molecular breeding, the difficulties include not only the limited number of DNA markers useful in the auxiliary selection, but also the inconsistence of the number and the significance of the quantitative traits loci (QTL). Therefore, since the genome sequencing of cabbages is not finished yet, and the study on functional genome study is gaining increasing interests, there is a need for a quick, sensitive and efficient qualitative analysis on the various traits in plant and the DNA profiles, and a quantitative analysis on the phenotypes in plant and changes in gene expressions, which is usefully in the breeding of drought-resistance cabbages.

There is a need in the art for identifying plant drought-resistance genes.

SUMMARY OF THE INVENTION

It is an objective of the current invention to provide for drought resistance in a plant. With plants provided with drought resistance, or plants with improved drought resistance it is e.g. possible to obtain higher yields of crop and/or plant product when the plant is subjected to a period or periods of drought when compared to plants not provided with (improved) drought resistance. It was found a plant can be provided with (improved) drought resistance when the expression in said plant of a JAZ5a gene is enhanced. The current invention thus provides for uses of the JAZ5a gene for providing (improved) drought resistance. Other aspects of the present invention will be apparent to the skilled person based on the contents disclosed herein.

DEFINITIONS

Figure 1:
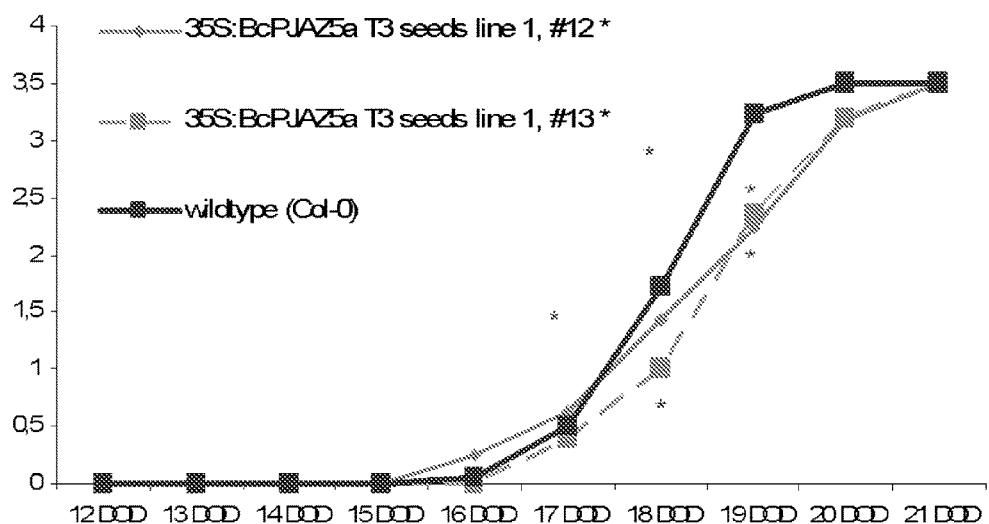
FIG. 1 shows wilting symptoms 15 DOD and onwards, plants were daily given a score between 0 and 4 (y-axis) based on which wilting symptoms they exhibited. Wilting symptoms were expressed as 0, no symptoms; 1, very mild loss of turgor; 2, loss of turgor; 3, severe loss of turgor; 4, putatively dead. Red asterisk indicate statistical differences in wilting score between mutant plants and wildtype plants (student's t-test; $\alpha<0.05$). Black asterisk in legend indicate hetorozygosity of the line. Each graph represents an individual tray.
Figure 1:
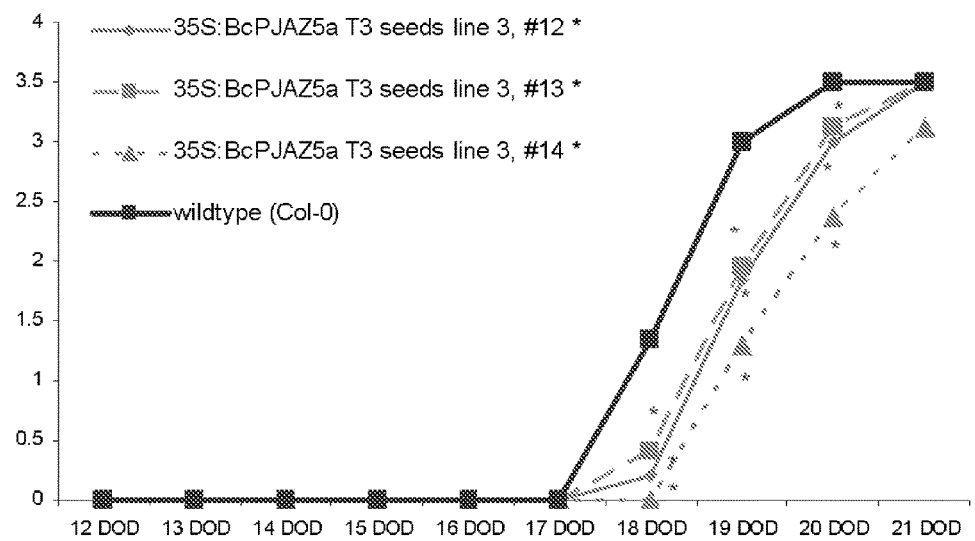
Figure 2:
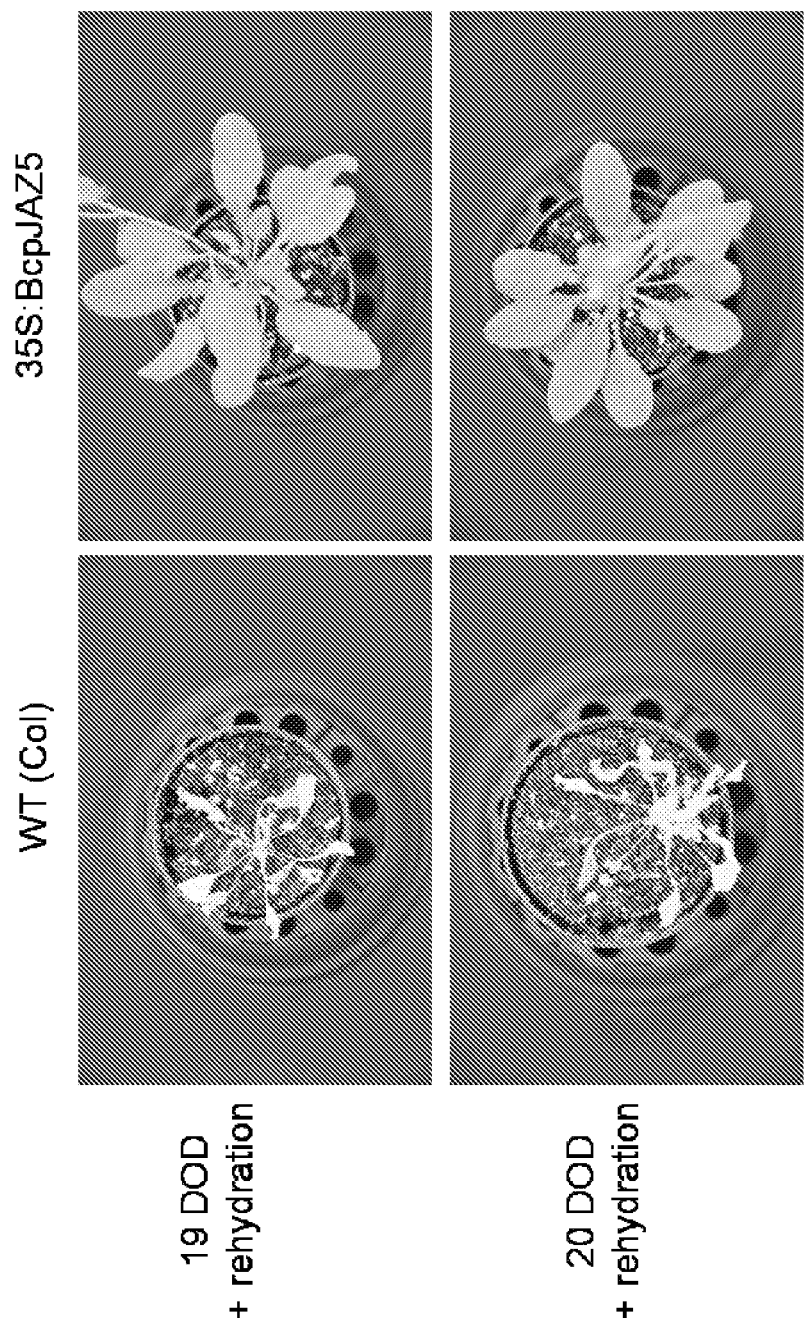
FIG. 2 shows a representative effect of rehydration one week after rehydration at 19 DOD or 20 DOD, comparing wild-type plants with 35:BcpJAZ5a plants. Clearly, the 35:BcpJAZ5a plants perform better than the wild-type plants.

In the following description and examples, a number of terms are used. In order to provide a clear and consistent understanding of the specification and claims, including the scope to be given to such terms, the following definitions are provided. Unless otherwise defined herein, all technical and scientific terms used have the same meaning as commonly understood by one of ordinary skill in the art to which this invention belongs. The disclosures of all publications, patent applications, patents and other references are incorporated herein in their entirety by reference.

Methods of carrying out the conventional techniques used in methods of the invention will be evident to the skilled worker. The practice of conventional techniques in molecular biology, biochemistry, computational chemistry, cell culture, recombinant DNA, bioinformatics, genomics, sequencing and related fields are well-known to those of skill in the art and are discussed, for example, in the following literature references: Sambrook et al., Molecular Cloning. A Laboratory Manual, 2nd Edition, Cold Spring Harbor Laboratory Press, Cold Spring Harbor, N.Y., 1989; Ausubel et al., Current Protocols in Molecular Biology, John Wiley & Sons, New York, 1987 and periodic updates; and the series Methods in Enzymology, Academic Press, San Diego.

In this document and in its claims, the verb "to comprise" and its conjugations is used in its non-limiting sense to mean that items following the word are included, but items not specifically mentioned are not excluded. As used herein, the term "comprising", "having" or "containing" includes "comprising", "consisting substantively of", "consisting essentially of", and "consisting of". The "consisting substantively of", "consisting essentially of" and "consisting of" are specific concepts of the generic terms "comprising", "having" and "containing".

As used herein, the singular forms "a," "an" and "the" include plural referents unless the context clearly dictates otherwise. For example, a method for isolating "a" DNA molecule, as used above, includes isolating a plurality of molecules (e.g. 10's, 100's, 1000's, 10's of thousands, 100's of thousands, millions, or more molecules).

The term "polynucleotide", "nucleic acid molecule" or "nucleic acid sequence" refers to a DNA or RNA molecule in single or double stranded form, particularly a DNA encoding a protein according to the invention. An "isolated nucleic acid sequence" refers to a nucleic acid sequence which is no longer in the natural environment from which it was isolated, e.g. the nucleic acid sequence in a bacterial host cell or in the plant nuclear or plastid genome. For example, a polynucleotide and a polypeptide in a natural state in the living cell is not isolated or purified. However, when the same polynucleotide or polypeptide is separated from the other substances with which it coexist in the said natural state, it is called "isolated" and/or "purified".

Aligning and alignment: With the term "aligning" and "alignment" is meant the comparison of two or more nucleotide sequences based on the presence of short or long stretches of identical or similar nucleotides. Several methods for alignment of nucleotide sequences are known in the art, as will be further explained below.

"Expression of a gene" refers to the process wherein a DNA region, which is operably linked to appropriate regulatory regions, particularly a promoter, is transcribed into an RNA, which is biologically active, e.g. which is capable of being translated into a biologically active protein or peptide or active peptide fragment. An active protein in certain embodiments refers to a protein being constitutively active. The coding sequence is preferably in sense-orientation and encodes a desired, biologically active protein or peptide, or an active peptide fragment.

"Functional", in relation to proteins (or variants, such as orthologs or mutants, and fragments), refers to the capability of a gene and/or encoded protein to have an effect on a quantitative and/or qualitative feature(s) of a plant. By modifying the expression level of the gene (e.g. by enhancing expression or reducing expression) the quantitative and/or qualitative feature of a plant is affected. For example, when a protein has a function in drought resistance, enhancing gene expression may lead to drought resistance. The skilled person will have no difficulties in testing functionality with regard to abiotic stresses such as drought.

The term "gene" means a DNA sequence comprising a region (transcribed region), which is transcribed into an RNA molecule (e.g. an mRNA) in a cell, operably linked to suitable regulatory regions (e.g. a promoter). A gene may thus comprise several operably linked sequences, such as a promoter, a 5' leader sequence comprising e.g. sequences involved in translation initiation, a (protein) coding region (cDNA or genomic DNA) and a 3' non-translated sequence comprising e.g. transcription termination sequence sites. A "chimeric gene" (or recombinant gene) refers to any gene, which is not normally found in nature in a species, in particular a gene in which one or more parts of the nucleic acid sequence are present that are not associated with each other in nature. For example the promoter is not associated in nature with part or all of the transcribed region or with another regulatory region. The term "chimeric gene" is understood to include expression constructs in which a promoter or transcription regulatory sequence is operably linked to one or more coding sequences or to an antisense (reverse complement of the sense strand) or inverted repeat sequence (sense and antisense, whereby the RNA transcript forms double stranded RNA upon transcription).

"Identity" is a measure of the identity of nucleotide sequences or amino acid sequences. In general, the sequences are aligned so that the highest order match is obtained. "Identity" per se has an art-recognized meaning and can be calculated using published techniques. See, e.g.: (COMPUTATIONAL MOLECULAR BIOLOGY, Lesk, A. M., ed., Oxford University Press, New York, 1988; BIO- COMPUTING: INFORMATICS AND GENOME PROJECTS, Smith, D. W., ed., Academic Press, New York, 1993; COMPUTER ANALYSIS OF SEQUENCE DATA, PART I, Griffin, A. M., and Griffin, H. G., eds., Humana Press, New Jersey, 1994; SEQUENCE ANALYSIS 1N MOLECULAR BIOLOGY, von Heinje, G., Academic Press, 1987; and SEQUENCE ANALYSIS PRIMER; Gribskov, M. and Devereux, J., eds., M Stockton Press, New York, 1991). While a number of methods exist to measure identity between two polynucleotide or polypeptide sequences, the term "identity" is well known to skilled artisans (Carillo, H., and Lipton, D., SIAM J. Applied Math (1988) 48:1073). Methods commonly employed to determine identity or similarity between two sequences include, but are not limited to, those disclosed in GUIDE TO HUGE COMPUTERS, Martin J. Bishop, ed., Academic Press, San Diego, 1994, and Carillo, H., and Lipton, D., SIAM J. Applied Math (1988) 48:1073. Methods to determine identity and similarity are codified in computer programs. Preferred computer program methods to determine identity and similarity between two sequences include, but are not limited to, GCS program package (Devereux, J., et al., Nucleic Acids Research (1984) 12(1):387), BLASTP, BLASTN, FASTA (Atschul, S. F. et al., J. Molec. Biol. (1990) 215:403).

As an illustration, by a polynucleotide having a nucleotide sequence having at least, for example, 95% "identity" to a reference nucleotide sequence encoding a polypeptide of a certain sequence it is intended that the nucleotide sequence of the polynucleotide is identical to the reference sequence except that the polynucleotide sequence may include up to five point mutations per each 100 nucleotides of the reference polypeptide sequence. In other words, to obtain a polynucleotide having a nucleotide sequence at least 95% identical to a reference nucleotide sequence, up to 5% of the nucleotides in the reference sequence may be deleted and/or substituted with another nucleotide, and/or a number of nucleotides up to 5% of the total nucleotides in the reference sequence may be inserted into the reference sequence. These mutations of the reference sequence may occur at the 5' or 3' terminal positions of the reference nucleotide sequence, or anywhere between those terminal positions, interspersed either individually among nucleotides in the reference sequence or in one or more contiguous groups within the reference sequence.

Similarly, by a polypeptide having an amino acid sequence having at least, for example, 95% "identity" to a reference amino acid sequence of SEQ ID NO: 1 is intended that the amino acid sequence of the polypeptide is identical to the reference sequence except that the polypeptide sequence may include up to five amino acid alterations per each 100 amino acids of the reference amino acid of SEQ ID NO: 1. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

A nucleic acid according to the present invention may include any polymer or oligomer of pyrimidine and purine bases, preferably cytosine, thymine, and uracil, and adenine and guanine, respectively (See Albert L. Lehninger, *Principles of Biochemistry*, at 793-800 (Worth Pub. 1982) which is herein incorporated by reference in its entirety for all purposes). The present invention contemplates any deoxyribonucleotide, ribonucleotide or peptide nucleic acid component, and any chemical variants thereof, such as methylated, hydroxymethylated or glycosylated forms of these bases, and the like. The polymers or oligomers may be heterogenous or homogenous in composition, and may be isolated from naturally occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

As used herein, the term "operably linked" refers to a linkage of polynucleotide elements in a functional relationship. A nucleic acid is "operably linked" when it is placed into a functional relationship with another nucleic acid sequence. For instance, a promoter, or rather a transcription regulatory sequence, is operably linked to a coding sequence if it affects the transcription of the coding sequence. Operably linked means that the DNA sequences being linked are typically contiguous and, where necessary to join two protein encoding regions, contiguous and in reading frame so as to produce a "chimeric protein". A "chimeric protein" or "hybrid protein" is a protein composed of various protein "domains" (or motifs) which is not found as such in nature but which a joined to form a functional protein, which displays the functionality of the joined domains. A chimeric protein may also be a fusion protein of two or more proteins occurring in nature. The term "domain" as used herein means any part(s) or domain(s) of the protein with a specific structure or function that can be transferred to another protein for providing a new hybrid protein with at least the functional characteristic of the domain.

"Plant" refers to either the whole plant or to parts of a plant, such as cells, tissue or organs (e.g. pollen, seeds, gametes, roots, leaves, flowers, flower buds, anthers, fruit, etc.) obtainable from the plant, as well as derivatives of any of these and progeny derived from such a plant by selfing or crossing. "Plant cell(s)" include protoplasts, gametes, suspension cultures, microspores, pollen grains, etc., either in isolation or within a tissue, organ or organism.

As used herein, the term "promoter" refers to a nucleic acid fragment that functions to control the transcription of one or more genes, located upstream with respect to the direction of transcription of the transcription initiation site of the gene, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one of skill in the art to act directly or indirectly to regulate the amount of transcription from the promoter. Optionally the term "promoter" includes herein also the 5'UTR region (5' Untranslated Region) (e.g. the promoter may herein include one or more parts upstream (5') of the translation initiation codon of a gene, as this region may have a role in regulating transcription and/or translation. A "constitutive" promoter is a promoter that is active in most tissues under most physiological and developmental conditions. An "inducible" promoter is a promoter that is physiologically (e.g. by external application of certain compounds) or developmentally regulated. A "tissue specific" promoter is only active in specific types of tissues or cells. A "promoter active in plants or plant cells" refers to the general capability of the promoter to drive transcription within a plant or plant cell. It does not make any implications about the spatio-temporal activity of the promoter.

The terms "protein" or "polypeptide" are used interchangeably and refer to molecules consisting of a chain of amino acids, without reference to a specific mode of action, size, 3 dimensional structure or origin. A "fragment" or "portion" of a protein may thus still be referred to as a "protein". An "isolated protein" is used to refer to a protein which is no longer in its natural environment, for example in vitro or in a recombinant bacterial or plant host cell.

A "genetically modified plant" refers herein to a plant or plant cell having been transformed, e.g. by the introduction of an exogenous gene or additional copy or copies of an endogenous gene, said exogenous gene or additional endogenous gene may be integrated into the genome. A transgenic plant cell transformed with an (isolated) polynucleotide sequence and plant cells and plants regenerated therefrom, are all understood to comprise said (isolated) polynucleotide sequence. A transgenic plant cell may refer to a plant cell in isolation or in tissue culture, or to a plant cell contained in a plant or in a differentiated organ or tissue, and both possibilities are specifically included herein. Hence, a reference to a plant cell in the description or claims is not meant to refer only to isolated cells or protoplasts in culture, but refers to any plant cell, wherever it may be located or in whatever type of plant tissue or organ it may be present. Methods for obtaining transgenic plant cells and plants are well known in the art and include but are not limited to *Agrobacterium*-mediated transformation of plant explants, particle bombardment of plant explants, transformation of plant explants using whiskers technology, transformation using viral vectors, electroporation of plant protoplasts, direct uptake of DNA by protoplasts using polyethylene glycol, microinjection of plant explants and/or protoplasts. *Agrobacterium*-mediated transformation is a preferred method to introduce the nucleic acid molecule of the invention into plant explants. *Agrobacterium tumefaciens* harbors a natural vector called Ti plasmid which was engineered to make it suitable for introduction of exogenous nucleic acid molecules into plant genomes. For genetic transformation, plant-derived explants are incubated with suspension of *Agrobacterium* cells followed by cultivation of the explants on the medium containing a selective agent that promotes growth and regeneration of the transformed cells only.

As used herein, the "isolated plant drought-resistance protein (polypeptide)", "isolated polypeptide that improves the plant drought-resistant ability", "isolated BccJAZ5a protein" or "isolated BccJAZ5a polypeptide" refers to the BccJAZ5a protein substantially free of the other proteins, lipids, saccharides and other substances that may be naturally associated with said protein. A skilled person in the art can utilize standard protein purification techniques to purify the BccJAZ5a protein. The substantially pure polypeptide forms a single major band on a non-reduced polyacrylamide gel.

DETAILED DESCRIPTION OF THE INVENTION

The present inventors have isolated for the first time a new plant drought-resistance gene from *Brassica* spp., which can be used to provide improved drought-resistance or drought resistance in a plant. The isolated gene is named as "BccJAZ5a", based on which, transgenic plants with improved drought-resistant ability can be produced.

The current invention relates to the improvement of drought resistance of a plant by modifying the expression of a gene in said plant. The improvement is relative to a plant in which such modification has not been introduced or is not present. Such plant is preferably of the same species and/or variety. In other words, a modified plant according to the invention is, in comparison to the non-modified plant, better able to grow and survive under conditions of less water availability, water-deprivation or conditions of drought.

Drought stress, i.e. a period of limited availability of suitable water as described above, may also manifest itself in a wilted state of the plant, i.e. in a state wherein a plant or part thereof has reduced turgor compared to a state wherein water is sufficiently available to the plant. In this regard, a modified plant with enhanced expression (for example with enhanced, derepressed, or insertion of a gene) and/or activity of the JAZ5a protein may be less wilted than a corresponding non-modified plant if exposed to drought stress for the same time period under the same conditions.

Limited availability of water or drought is to be understood as a situation wherein water is or may become a limiting factor for biomass accumulation or crop yield for a non-transformed or naturally occurring plant grown under such condition. For a plant obtained according to a method according to the present invention and grown under said condition, water may not, or to a lesser degree, be a limiting factor.

It is believed by the current inventors that by enhancing expression (e.g. by enhancing, derepression or insertion of a gene) of JAZ5a leads to the presence (or increased presence) of functional JAZ5a protein, either as the consequence of high expression or as the consequence of increased activity/functionality of the JAZ5a protein, or both, and that said presence (or increased presence) of functional JAZ5a protein leads to decreased need for water and/or improved resistance to drought of said plant In one embodiment the use is provided of a protein for providing a plant with drought resistance, wherein the protein is:

(a) a protein having the amino acid sequence of SEQ ID NO:4; or (b) a protein derived from the protein of (a) by substitution, deletion or addition of one or more residues in the amino acid sequence of SEQ ID NO:4 and wherein the protein is functionally equivalent to the amino acid sequence represented by SEQ ID NO:4; or (c) a protein having at least 60% identity to the amino acid sequence of SEQ ID NO:4 and having the same function as that of the amino acid sequence represented by SEQ ID NO:4.

In one embodiment, the said plant drought-resistance protein has at least 60%, 65%, 70%, 75%, 80%, 85%, 90%, 92%, 95%, 96%, 97%, 98% or 99% identity with the amino acid sequence represented by SEQ ID NO:4.

In one embodiment, the plant drought-resistance protein has 1-20, preferably 1-10, more preferable 1-5, most preferably 1-3 residues substituted, deleted or added in the amino acid sequence of SEQ ID No:4.

In one embodiment, the plant is a plant of Cruciferae. In one embodiment, the Cruciferae plant is selected from the group consisting of *Brassica* spp. plant and *Abrabidopsis* spp. plant. In one embodiment, the *Brassica* spp. plant is *Brassica campestris* ssp. *pekinensis.*

In one embodiment, the *Abrabidopsis* spp. plant is *Arabidopsis thaliana* (L.) *Heynh*. In one embodiment, the plant drought-resistance protein is derived from the *Brassica* spp. Plant, preferably derived from *Brassica campestris* L. ssp. *chinensis*.

In one embodiment, the use of a polynucleotide is provided for providing a plant with drought resistance, which is selected from the group consisting of:
(i) a polynucleotide encoding said protein; or
(ii) a polynucleotide complementary to the polynucleotide of (i).

In one embodiment, the nucleotide sequence of said polynucleotide is set forth in SEQ ID NO: 1 or 2. In an embodiment, a chimeric gene is provided comprising such polynucleotide. In one embodiment, a vector is provided, which contains said polynucleotide. Said vector may be chosen based on the host cell or host plant used. One of ordinary skill in the art is capable of selecting a suitable vector for a specified host cell.

It is clear to the person skilled in the art that genes, including the polynucleotides of the invention, can be cloned on basis of the available nucleotide sequence information, such as found in the attached sequence listing, by methods known in the art. These include e.g. the design of DNA primers representing the flanking sequences of such gene of which one is generated in sense orientations and which initiates synthesis of the sense strand and the other is created in reverse complementary fashion and generates the antisense strand. Thermo stable DNA polymerases such as those used in polymerase chain reaction are commonly used to carry out such experiments. Alternatively, DNA sequences representing genes can be chemically synthesized and subsequently introduced in DNA vector molecules that can be multiplied by e.g. compatible bacteria such as e.g. *E. coli*.

In one embodiment, a genetically engineered host cell is provided, which comprises said vector or which comprises said polynucleotide integrated in the genome. In one embodiment, a plant is provided, which comprises any of the aforementioned polynucleotides.

In one embodiment, a method for preparing the aforementioned protein is provided, which comprises:
(a) culturing said host cell under conditions suitable for expression;
(b) isolating said protein from the culture.

In one embodiment, the use is provided of the aforementioned protein or a polynucleotide encoding said protein for providing a plant with (improved) drought-resistance. In one embodiment, the use is for providing a plant with (improved) drought-resistance in the bolting stage.

In one embodiment, a method for providing a plant with improved drought resistance is provided, which comprises enhancing the expression or activity of the aforementioned protein in said plant. In one embodiment, said method comprises transforming a polynucleotide encoding the aforementioned protein into the genome of the plant. In one embodiment, said method comprises:
(1) providing an *Agrobacterium* an expression vector comprising a polynucleotide encoding the protein of the invention;
(2) providing a plant cell, organ or tissue;
(3) contacting the plant cell, organ or tissue of step (2) with the *Agrobacterium* of step (1), such that the polynucleotide encoding the protein of the invention is introduced into the plant cell
(3) optionally, selecting the plant cell, organ or tissue into which the polynucleotide encoding the protein of the invention was introduced;
(4) regenerating the plant cell, organ or tissue of step (3) into a plant.

In one embodiment, the polynucleotide encoding the protein of the invention is integrated into the chromosome of the plant cell.

In one embodiment a genetically modified plant is provided comprising a polynucleotide encoding the plant drought-resistance protein of the invention.

In one embodiment of the present invention, a molecular marker for identifying drought-resistance in a plant is provided, wherein said molecular marker comprises at least 30, 35, 40, 45, 50, or more (contiguous) nucleotides of the sequence of SEQ ID. No 1 or 2. In one embodiment, a method is provided for identifying such molecular marker, said method comprising the step of sequencing the DNA of a plant cell. In one embodiment, a method for identifying such molecular marker is provided comprising the step of amplifying the said sequence of SEQ ID No. 1 or 2 and detecting the amplicon. In one embodiment, a pair of primers is provided capable of amplifying the said sequence of SEQ ID No. 1 or 2, in a further embodiment, the pair of primers provided is represented by the nucleotide sequences SEQ ID NO: 5 and 6.

There is no specific limitation on the plants that can be used in the present invention, as long as the plant can be transformed, e.g. using a gene, chimeric gene or vector. The plants include various crops, flower plants or plants of forestry, etc. Specifically, the plants include, but are not limited to, dicotyledon, monocotyledon or gymnosperm. More specifically, the plants include, but is not limited to, wheat, barley, rye, rice, corn, sorghum, beet, apple, pear, plum, peach, apricot, cherry, strawberry, *Rubus* swinhoei Hance, blackberry, bean, lentil, pea, soy, rape, mustard, opium poppy, *olea europea, helianthus*, coconut, plant producing castor oil, cacao, peanut, calabash, cucumber, watermelon, cotton, flax, *cannabis*, jute, citrus, lemon, grapefruit, spinach, lettuce, asparagus, cabbage, *Brassica campestris* L. ssp. *Pekinensis, Brassica campestris* L. ssp. *chinensis*, carrot, onion, murphy, tomato, green pepper, avocado, *cassia*, camphor, tobacco, nut, coffee, aubergine, sugar cane, tea, pepper, grapevine, nettle grass, banana, natural rubber tree and ornamental plant, etc.

The term "plant(s)" includes, but is not limited to, plants of Cruciferae, Gramineae and Rosaceae. For example, the "plant" includes but is not limited to *Brassica campestris* L. ssp. *Pekinensis* and *Brassica campestris* L. ssp. *chinensis* of *Brassica* spp. of the Cruciferae; *Abrabidopsis* spp. plant of the Cruciferae; rice of Gramineae; and tobacco, melon and fruit, vegetable, rape and the like. More preferably, the "plant" is a plant of the *Brassica* spp. or *Abrabidopsis* spp. of the Cruciferae.

The polypeptide of the present invention can be a recombinant polypeptide, a natural polypeptide or a synthetic polypeptide. Preferably, it is a recombinant polypeptide. The polypeptide of the present invention can be a product purified from a natural source, chemically synthesized, or recombinantly produced by prokaryotic or eukaryotic hosts (such as, bacterium, yeast, higher plant, insect and mammalian cell). According to the host used in the recombinant production, the polypeptide of the present invention can be glycosylated or non-glycosylated. The polypeptide of the current invention can further include or not include the first native methionine residue.

The present invention further includes fragments, derivatives and analogs of the BccJAZ5a protein. As used herein, the terms "fragment", "derivative" and "analog" refer to the polypeptide that have substantively the same biological function and/or activity of the BccJAZ5a protein of the present invention. The polypeptide fragment, derivative or analog of the present invention may be (i) a polypeptide in which one or several conservative (preferred) or non-conservative amino acid residues are substituted by one or more amino acid residues that are genetically encoded or not, or (ii) a polypeptide with one or more amino acid residues bearing a substituent, or (iii) a fusion polypeptide of the mature polypeptide and another compound (such as a compound for extending the half life of the polypeptide, such as polyethylene glycol), or (iv) a polypeptide formed by an additional amino acid sequence (such as a leader sequence or a secretion sequence, or a sequence facilitating purification, or a proteinogen sequence, or a fusion protein) fusing to the polypeptide sequence. According to the definitions provided herein, these fragments, derivatives and analogs can be understood by the skilled in the art.

As used herein, the term "BccJAZ5a protein" refers to a polypeptide providing improved drought-resistance or drought-resistance to plants based on the sequence of SEQ ID NO:4. This term also includes variants of SEQ ID NO:4 that provide (improved) plant drought-resistance ability. Mutations include but are not limited to deletion, insertion and/or substitution of one or more (generally 1-50, preferably 1-30, more preferably 1-20, most preferably 1-10, further more preferably 1-8 or 1-5) amino acids, and addition or deletion of one or more (generally within 20, preferably within 10, more preferably within 5) amino acids at the C-terminus and/or N-terminus. For example, it is understood that substitution with an amino acid residue having close or similar property will generally not affect the function of the protein. Further, for example, addition or deletion of one or more amino acids from the C-terminus and/or N-terminus will generally not affect the function of the protein. The term also includes the active fragments and active derivatives of the BccJAZ5a protein.

Variants of the polypeptide include its homologous sequences, conservative mutants, allelic mutant, natural mutant, induced mutant, protein encoded by a DNA that could hybridize to the DNA of BccJAZ5a protein under a high or low stringent condition, and polypeptide or protein obtained by utilizing an anti-serum against the BccJAZ5a protein. The present invention also provides more related polypeptides, such as fusion proteins containing BccJAZ5a protein or fragments thereof. In addition to the full-length or almost full-length polypeptides, the present invention also includes the soluble fragments of the BccJAZ5a protein. Generally, the fragment contains at least about 20, generally at least about 30, preferably at least about 50, more preferably at least about 80, most preferably at least about 100 continuous amino acid of the BccJAZ5a protein.

The present invention also provides analogs of the BccJAZ5a protein or polypeptide. These analogs may be different from the native BccJAZ5a protein in the primary sequence or in modification patters along the same primary sequence, or both. These polypeptides include the natural or induced genetic mutants. The induced mutants may be obtained via various techniques, for example, by radiation or by exposure to a mutagen so as to produce a random mutagenesis. They may also be obtained by site-directed mutagenesis or some other known biological technologies. The analogs also include those having residues different from the natural L-amino acid (such as D-amino acid), and those having un-natural or synthetic amino acid(s), such as β- and γ-amino acids. It should be understood that the polypeptide of the subject invention is not limited to the above representative examples.

Modification patterns, which will not change the primary structure, include in vivo or in vitro chemical derivation, such as acetylation or carboxylation. Modification may also be glycosylation. Modification may also be phosphorylation of the amino acid residues (such as, phosphorylated tyrosine, phosphorylated serine, and phosphorylated threonine) in the sequence. Also included are polypeptides which are modified to have an improved anti-proteolysis property or optimize the solubility property.

In the present invention, "a conservative mutant of BccJAZ5a protein" refers to a polypeptide having up to 20, preferably up to 10, more preferably up to 5, most preferably up to 3 amino acids in the amino acid sequence of SEQ ID NO:4 being replaced by the amino acids with similar or close property. These mutant polypeptides preferably are produced according to the amino acid replacement shown below in Table 1.

TABLE 1

| Amino acid residue | Representative substitution | Preferred substitution |
|---|---|---|
| Ala (A) | Val; Leu; Ile | Val |
| Arg (R) | Lys; Gln; Asn | Lys |
| Asn (N) | Gln; His; Lys; Arg | Gln |
| Asp (D) | Glu | Glu |
| Cys (C) | Ser | Ser |
| Gln (Q) | Asn | Asn |
| Glu (E) | Asp | Asp |
| Gly (G) | Pro; Ala | Ala |
| His (H) | Asn; Gln; Lys; Arg | Arg |
| Ile (I) | Leu; Val; Met; Ala; Phe | Leu |
| Leu (L) | Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Leu |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala | Leu |

The present invention further provides polynucleotide sequences encoding the BccJAZ5a protein of the current invention or variant polypeptides thereof.

The polynucleotides of the present invention may be DNA or RNA molecules. The DNA molecules include cDNA, genomic DNA and synthetic DNA. The DNA molecules may be in the form of a single strand or of double strands. The DNA molecule may be the coding strand or the non-coding strand. The coding sequence encoding the mature polypeptide may be identical to the coding sequence of SEQ ID NO: 1 or 2, or may be their degeneration variants. As used therein, "a degeneration variant" refers to a nucleic acid molecule that encodes a protein having the sequence of SEQ ID NO: 4 with a nucleotide sequence different from the coding sequence as set forth in SEQ ID NO: 1 or 2. The polynucleotides encoding polypeptide of SEQ ID NO:4 may comprise a coding sequence only encoding the mature polypeptide; a coding sequence of the mature polypeptide and an additional coding sequence; the coding sequence of the mature polypeptide and a non-coding sequence, optionally as well as an additional coding sequence.

The term "polynucleotide encoding a polypeptide" may optionally include, in addition to the polynucleotide encoding said polypeptide, an additional coding and/or a non-coding polynucleotide.

The present invention further relates to variants of the above polynucleotides, which encode the same amino acid sequence of the polypeptide of the present invention, and fragments, analogs and derivatives thereof. The variants of the polynucleotides may be the naturally occurring allelic mutants or non-naturally occurring mutants. The nucleotide variants include substitution variants, deletion variants and insertion variants. As known in the prior art, an allelic variant is an alternative form of a polynucleotide, wherein the mutation may be substitution, deletion or insertion of one or more nucleotides, but the function of the polypeptide encoded by the allelic variant is substantively un-altered.

The present invention also relates to a polynucleotide hybridizing to any of the above sequences and having at least 50%, preferably at least 70%, more preferably at least 80% sequence identity between the two sequences. The present invention specifically relates to a polynucleotide hybridizing to the polynucleotides of the present invention under stringent conditions. In the present invention, the "stringent condition" refers to: (1) hybridization and elution at a relatively lower ionic strength and relatively higher temperature, such as 0.2×SSC, 0.1% SDS, 60° C.; or (2) presence of denaturation agent during hybridization, such 50% (v/v) formamide, 0.1% calf serum/0.1% Ficoll, 42° C., and the like; or (3) conditions only allowing hybridization between two sequences that have at least 80%, preferably at least 90%, more preferably at least 95% identity. Moreover, the polypeptide encoded by the hybridizing polynucleotide exhibits the same biological function and activity as those of the mature polypeptide as shown in SEQ ID NO: 4.

The present invention also relates to nucleic acid fragments that can hybridize to the any of the above sequences. As used herein, a "nucleic acid fragment" contains at least 15 nucleotides, preferably at least 30 nucleotides, more preferably at least 50 nucleotides, most preferably at least 100 nucleotides. The fragment of nucleic acid may be used in the amplification technique of nucleic acid (such as PCR) to determine and/or isolate the polynucleotide encoding the BccJAZ5a protein.

The full-length nucleotide sequence of the BccJAZ5a protein of the present invention or fragment thereof can typically be prepared via PCR amplification method, recombinant method or artificial synthesis. As to PCR amplification, the sequences of interests can be amplified by designing primers according to the related nucleotide sequence disclosed in the present invention, e.g. the open-reading frame, and using a commercially available cDNA library or a cDNA library prepared according to any of the conventional methods known in the art as a template. For a large sequence, two or more PCR amplications may be needed, the fragments obtained in each amplification may be fused together, e.g. via ligation, in a correct orientation.

Once the sequence is obtained, it can be produced in a large amount using recombinant techniques. The sequence may be cloned into a vector. The vector can be transformed into a cell, and then the sequence can be isolated from proliferated host cells using conventional means.

Furthermore, the related sequence can be synthesized by artificial synthesis, especially when the fragment is relatively short. Generally, several small fragments are first synthesized and then fuseg, e.g. via ligation or fusion PCR, into a large fragment. The DNA sequence encoding the protein (or fragment, or variant, or derivative thereof) of the present invention can be prepared via chemical synthesis. The obtained DNA sequence can be incorporated into various known DNA molecules (such as vectors) and then into cells. Further, mutations can be introduced into the protein sequence (i.e. the sequence encoding the protein sequence) of the present invention through the chemical synthesis.

The present invention also relates to a vector comprising the polynucleotide of the present invention, a host cell genetically engineered to comprise the vector or the coding sequence of the BccJAZ5a protein of the present invention, and a method for recombinantly producing the polypeptide of the present invention.

The polynucleotide of the present invention can be used to express or produce a recombinant BccJAZ5a protein using conventional recombinant DNA techniques. The following steps may be included in such a use:

(1) Transforming or transfecting a host cell with a polynucleotide (or its variant) encoding the BccJAZ5a protein of the present invention, or a recombinant expression vector comprising said polynucleotide;

(2) culturing the host cell in a culture medium;

(3) isolating and purifying the protein from the culture medium or the cultured cells.

In the present invention, the polynucleotide sequence of the BccJAZ5a protein can be inserted into a recombinant expression vector. The term "recombinant expression vector" refers to a bacterial plasmid, phage, yeast plasmid, plant cell virus, mammalian cell virus and any other vectors known in the art. In summary, any plasmids and vectors can be used as long as they can replicate and retain stably in the host. Expression vectors can contain a replication origin, promoter, markers and translation control element.

Various methods known in the art can be used to construct an expression vector containing a DNA sequence encoding the BccJAZ5a protein and transcription/translation regulatory signals. These methods include in vitro recombinant techniques, DNA synthesis, in vivo recombinant techniques, etc. The DNA sequence may be operably linked under a promoter for directing mRNA synthesis in the expression vector. The expression vector can further include a ribosome binding site for initiating the translation and a transcription terminator.

Further, the expression vector can contain one or more selectively labeled genes to provide phenotypic traits for selecting the transformed host cells. The labeled genes may encode, for example, dihydrofolate reductase, neomycin resistance and green fluorescent protein (GFP) for culture of eukaryotic cells, and kanamycin or ampicillin resistance for *E. coli*.

The vector comprising the above DNA sequence and suitable promoter or regulatory sequence can be used to transform host cells for protein expression.

The host cell may be a prokaryotic cell, such as bacterial cell; or lower eukaryotic cell, such as yeast cell; or higher eukaryotic cell, such as plant cell. Examples include *E. coli, Streptomyces, Agrobacterium*, fungi cell such as yeast, and plant cell, etc.

When expressing the polynucleotide of the present invention in a higher eukaryotic cell, the transcription can be enhanced when an enhancer sequence is inserted into the vector. The enhancer may be a cis-acting factor of DNA, which may contain about 10 to 300 bp and acts on a promoter to enhance the transcription of the gene.

The person skilled in the art knows how to select a vector, promoter, enhancer and host cell.

Transformation of a host cell with the recombinant DNA can be carried out using conventional techniques known by the person skilled in the art. When the hosts are prokaryotic cells, such as *E. coli*, the competent cells that can uptake the DNA may be harvested after the exponential growth phase and then treated by $CaCl_2$ method, according methods known in the art. Another method is to use $MgCl_2$. If desired, the transformation could be conducted using electroporation. When the host cell is of an eukaryotic origin, one or more of the following DNA transfecting methods may be used: calcium phosphate precipitation, conventional mechanical method such as micro-injection, electroporation, liposome packing, etc. Transformation of plant may also be achieved by using *agrobacterium* or gene gun transformation, and the like, such as leaf discs transformation, rice immature embryo transformation, etc. The transformed plant cell, tissue or organ can be regenerated into a plant via conventional methods, so as to obtain a plant having altered traits.

The transformant may be cultured in conventional ways to express the polypeptide encoded by the gene of the present invention. Depending on the host cell used, the culture medium used in the culture may be selected from various (conventional) culture mediums. Culturing can be carried out under conditions suitable for growth of the host cell. When the host cell grows to a suitable density, the selected promoter may be induced by a suitable method (e.g. a temperature change or chemical induction), after which the cell may be further cultured for a period of time.

In the above methods, the recombinant polypeptide can be expressed in the cell, or on the cell membrane, or be secreted outside the cell. If desired, the recombinant protein could be isolated and purified via various isolation methods by utilizing the physical, chemical or other properties of the protein. These methods are well known in the art. Examples include but are not limited to the conventional renaturation treatment, treatment with protein precipitant (such as salting out), centrifugation, osmosis (for disrupting the bacterium), ultra-treatment, ultra-centrifugation, molecular sieve chromatography (gel filtration), adsorption chromatography, ion-exchange chromatography, liquid chromatography such as high performance liquid chromatography (HPLC) and the other, and combinations thereof.

The recombinant BccJAZ5a can be used in many applications. For example, it can be used to screen for the antibody, polypeptide or the other ligands agonistic or antagonistic to the function of the BccJAZ5a protein. Screening a polypeptide library with the expressed recombinant BccJAZ5a protein may help finding valuable polypeptide molecules that could inhibit or stimulate the function of the BccJAZ5a protein.

The whole polynucleotide of the present invention or a portion thereof can be used as a probe, which may be fixed onto a microarray or a DNA chip (also termed as "gene chip") to perform an analysis of gene differential expression. Primers specific for the BccJAZ5a protein to perform RNA reverse transcription polymerase chain reaction (RT-PCR) for in vitro amplification can also be used to detect the transcription products of the BccJAZ5a protein.

The present invention also relates to a method for modifying a plant (to provide improved drought-resistance or drought resistance to the plant), comprising enhancing or providing the expression of the BccJAZ5a gene or the activity of encoded protein in the plant.

Methods for enhancing or providing the expression of the BccJAZ5a gene are well known in the art. For example, plants can be transformed with an expression construct carrying the BccJAZ5a coding gene to express the BccJAZ5a gene. A promoter can be used to enhance the expression of the BccJAZ5a gene. An enhancer (e.g. the first intron of the rice waxy gene or the first intron of the Actin gene, and the like) can be used to enhance the expression of the BccJAZ5a gene. Promoters that may be used in the current invention include but is not limited to the 35S promoter and the Ubi promoter in rice and corn.

In one embodiment of the present invention, a method for obtaining a plant with enhanced expression of BccJAZ5a protein includes:

(1) providing an *Agrobacterium* strain comprising an expression vector, wherein the expression vector contains a polynucleotide encoding a BccJAZ5a protein;

(2) contacting a plant cell, tissue or organ with the *Agrobacterium* of step (1) such that the polynucleotide encoding the BccJAZ5a protein is transferred into the plant cell and may be integrated into the genome, thereby transforming the plant cell;

(3) optionally, selecting the plant cell or tissue transformed with the polynucleotide encoding the BccJAZ5a protein; and (4) regenerating the plant cell or tissue of step (3) into a plant.

Any suitable conventional means, including reagents, temperature and pressure controls, can be used in this process.

The present invention also includes agonists to the BccJAZ5a protein or a polynucleotide encoding the BccJAZ5a protein of the invention. Since the agonists of the BccJAZ5a protein can regulate the activity or expression of the BccJAZ5a protein, the said agonists can also provide drought-resistance or improvements thereof to a plant through affecting the BccJAZ5a protein, to achieve improvements on traits.

The agonists of the BccJAZ5a protein may refer to any substance that can enhance the activity of BccJAZ5a, maintain the stability of BccJAZ5a, promote the expression of BccJAZ5a, prolong effect duration of BccJAZ5a, or promote transcription and translation of BccJAZ5a. These substances can be used in the present invention as agents for enhancing the drought-resistance of a plant.

In one embodiment of the present invention, a BccJAZ5a gene is provided, the genomic sequence of which is listed in SEQ ID NO: 1, and the cDNA sequence of which is indicated in SEQ ID NO: 2. Said gene encodes a protein containing 270 amino acids (SEQ ID NO:4). Said BccJAZ5a gene provides a new route for drought tolerance modification of plant.

The present invention will be further illustrated in combination with the examples below. It should be understood that these examples are for illustrating the present invention, but not be understood to limit the scope of the present invention in any way. The experimental methods, wherein specific conditions are not indicated in the following examples are performed using conventional conditions, such as those described in Sambrook et al., Molecular Cloning: A Laboratory Manual (New York: Cold Spring Harbor Laboratory Press, 2002), or according to the conditions recommended by the manufacturer. Unless otherwise specifically indicated, the percentage and part are calculated based on weight. Unless otherwise specifically indicated, all of the scientific terms used herein have the same meanings as those familiar to the skilled in the art. Furthermore, any methods and materials equivalent to the disclosed contents can be used in the present invention. The preferred practicing method and material disclosed herein are just for illustrative purpose.

All references cited in the present invention are incorporated herein by reference as each one of them was individually cited. Further, it is understood that various modifications and/or changes are obvious to a skilled person in the art, in view of above teaching of the current invention, falling within the scope as defined by the description and the claims.

SEQUENCE LISTING

SEQ ID NO. 1: genomic DNA sequence encoding the BccJAZ5a protein
SEQ ID NO. 2: cDNA sequence encoding the BccJAZ5a protein
SEQ ID NO. 3: genomic DNA sequence encoding the BccJAZ5b protein
SEQ ID NO. 4: amino acid sequence of the BccJAZ5a protein
SEQ ID NO. 5: forward primer 5' AAGAAGCCAAGTCT-GTGA 3'
SEQ ID NO. 6: reverse primer 5' TCGGAGGATAATGAT-GAC 3'

EXAMPLES

Segregating T3 progeny (harvested from 6 individual plants) from two individual transformation events of *Arabidopsis thaliana* (At) with the BccJAZ5a encoding nucleotide sequence from *Brassica rapa* ssp. *chinensis* behind a constitutive 35S promoter (35S::BccJAZ5a) (hereafter referred to as mutant seeds or mutant plants) were obtained from the National Laboratory of Plant Molecular Genetics, Shanghai Institute of Plant Physiology and Ecology, Shanghai Institutes for Biological Sciences, Chinese Academy of Sciences, 300 Fenglin Road, Shanghai 200032, China. As control At Col-0 (Columbia, N60000; hereafter referred to as control seed or plant) were obtained from the Nottingham *Arabidopsis* Stock Centre (NASC; School of Biosciences, University of Nottingham, Sutton Bonington Campus, Loughborough, LE12 5RD United Kingdom).

KeyGene N.V. and the Shanghai Institutes for Biological Sciences are parties to a joint research agreement.

For the gene "BccJAZ5" of the present invention two genomic sequences are provided, which respectively are BccJAZ5a (copy a) and BccJAZ5b (copy b). The genomic sequence of BccJAZ5a is indicated in SEQ ID NO:1, its CDS sequence is indicated in SEQ ID NO:2. It encodes a protein "BccJAZ5a" having 270aa (SEQ ID NO:4). The genomic sequence of BccJAZ5b is shown in SEQ ID NO:3.

The expression of BccJAZa from *Brassica rapa* ssp. *chinensis* was confirmed with a semi-quantitative RT-PCR. Primers used were:

```
BccJAZ5a:
Forward:  5' AAGAAGCCAAGTCTGTGA 3';(SEQ ID NO: 5)

Reverse:  5' TCGGAGGATAATGATGAC 3'.(SEQ ID NO: 6)
```

Growth Medium:

A soil mixture comprising one part of sand, one part of vermiculite and two parts of compost was used (sand: vermiculite:compost=1:1:2). This mixture increases the water percolation hence facilitates uniform water uptake by each pot and better water drainage. Before sowing, the seeds were kept at 4° C. for 3 days under dark and humid conditions for stratification.

Both mutant and control seeds were sown in 60-ml baskets (ARABASKETS, Lehle seeds) with a density of 1 plant per pot. For each genotype, there were 20 replicates. Baskets were kept in a rectangular tray containing 8×5=40 holes of ~4 cm diameter. Plants were cultivated in a growth chamber with a 16-hrs day (24° C.) and 8-hrs night (20° C.) at 60-70% relative humidity. The first 3 days after sowing the plants were kept at 100% humidity by covering them with transparent lids or transparent plastic bags. Nutrient solution (EC=1.5) was supplied to all the plants from the bottom of the pots in the tray 10 days after germination (DAG), and at 15 DAG the plants were subjected to drought (for 19, 20, or 21 days) by transferring the pots to dry trays. Subsequently, plants were rehydrated and observed for recovery after 1 week.

Replicates of individually harvested mutant T3 progeny from two individual transformation events and replicates of control plants were included. Total time needed for a complete test was approx. 36-39 days.

Drought Assay Examination

At 10 DAG, plants received nutrition (EC-1.5) and at 15 DAG each pot was moved to a dry tray. From this day onwards the plants did not receive any water. While water was withheld pots were shuffled daily within the trays to reduce the position effects and allow uniform evaporation. Every day the plants, especially the control (or wild type) (Col-0) were observed for wilting signs (see FIG. 1). On the $19^{th}$ day of drought (DOD), Col-0 wilted completely and did not recover upon rehydration. We determined this day as its permanent wilting point (PWP). From this day onwards replicates from the mutant were rehydrated and observed for recovery signs and pictures were taken (see FIG. 2). Mutant plants showed survival for at least 1 day longer under drought than did the control.

TABLE 2

Survival after rehydration. Batches of plants were rehydrated from 19 DOD onwards. Representative replicas were chosen to be actually rehydrated. Column $1^{st}$, $2^{nd}$, $3^{rd}$ DOR (day of rehydration) contains the data that indicates the ratio of plants that survived and the plants that died.

| Line | 1 DOR (19 DOD) | 2 DOR (20 DOD | 3 DOR (21 DOD) |
|---|---|---|---|
| 35S:BcPJAZ5a T3 seeds line 1, #12 | 1:1 | 2:2 | 0:4 |
| 35S:BcPJAZ5a T3 seeds line 1, #13 | 1:1 | 1:3 | 0:4 |
| Col-0 | 0:2 | 0:4 | 0:4 |
| 35S:BcPJAZ5a T3 seeds line 3, #12 | 2:0 | 2:2 | 0:4 |
| 35S:BcPJAZ5a T3 seeds line 3, #13 | 2:0 | 1:3 | 0:4 |
| 35S:BcPJAZ5a T3 seeds line 3, #14 | 2:0 | 3:1 | 1:3 |
| Col-0 | 1:1 | 0:4 | 0:4 |

Study on the Domains in the JAZ5a Protein, its Variants and Functions

The inventors of the subject application have identified domains in the BccJAZ5a protein (SEQ ID NO:4). Positions 101-130 constitute a tify domain, and the segment of 184-209 is a CCT_2 motif. These domains may be important active sites for the protein's drought-resistance function.

Based on the above analysis, the inventors construct several variants of the BccJAZ5a protein as specified below:

In the sequence of the BccJAZ5a protein (SEQ ID NO:4), amino acid 9 is changed from A to V, so as to obtain BccJAZ5a-M1 variant.

In the sequence of the BccJAZ5a protein (SEQ ID NO:4), amino acid 253 is changed from L to I, so as to obtain BccJAZ5a-M2 variant.

In the sequence of the BccJAZ5a protein (SEQ ID NO:4), amino acid 147 is changed from V to A, so as to obtain BccJAZ5a-M3 variant, and amino acid 230 is changed from L to I.

In the sequence of the BccJAZ5a protein (SEQ ID NO:4), amino acids 266-270 are deleted, so as to obtain BccJAZ5a-M4 variant.
In the sequence of the BccJAZ5a protein (SEQ ID NO:4), amino acids 159-161 are deleted, so as to obtain BccJAZ5a-M5 variant.
In the sequence of the BccJAZ5a protein (SEQ ID NO:4), four amino acids ATAA are added to the C-terminus, so as to obtain BccJAZ5a-M6 variant.

The CDS sequence of the BccJAZ5a gene shown in SEQ ID NO: 2 is first cloned into the pCAMBIA1300 vector at the Kpn I site to obtain a recombinant vector containing said CDS. Then, site-directed mutagenesis is conducted to introduce the corresponding substitution, deletion and addition to obtain the recombinant vectors containing the above-said variants respectively.

The recombinant vectors thus constructed are transformed into strains of *agrobacterium*, and then the *agrobacterium* strains are used to transform *Arabidopsis*, so that transgenic *Arabidopsis* plants are obtained. A drought treatment such as described above is used to verify the phenotype of these transgenic *Arabidopsis* plants. The transgenic plants show improved drought resistance as compared the wild type plants.

The invention claimed is:

1. A method for improving drought resistance in a plant that is not *Arabidopsis thaliana*, comprising introducing into the plant or enhancing expression or activity in the plant of a drought-resistance protein of plant origin having the amino acid sequence of SEQ ID NO:4 or at least 95% sequence identity to the amino acid sequence of SEQ ID NO:4.

2. The method according to claim 1, wherein the step of introducing into the plant or enhancing expression or activity in the plant of the drought-resistance protein comprises transforming said plant with a polynucleotide encoding the drought-resistance protein.

3. The method according to claim 2, wherein the polynucleotide is incorporated into the genome of the plant.

4. The method according to claim 2, comprising:
(1) providing an *Agrobacterium* strain containing an expression vector comprising a polynucleotide encoding the drought-resistance protein;
(2) providing a plant cell, organ or tissue;
(3) contacting the plant cell, organ or tissue of step (2) with the *Agrobacterium* strain of step (1) such that the polynucleotide encoding the drought-resistance protein is introduced into the plant cell, organ or tissue;
(4) optionally, selecting a plant cell;
(5) growing the plant cell, organ or tissue into a plant.

5. The method according to claim 4, wherein after introduction of the polynucleotide in the plant cell, organ or tissue, the polynucleotide integrates in the genome of the plant cell, organ or tissue.

6. The method according to claim 3, comprising:
(1) providing an *Agrobacterium* strain containing an expression vector comprising a polynucleotide encoding the drought-resistance protein;
(2) providing a plant cell, organ or tissue;
(3) contacting the plant cell, organ or tissue of step (2) with the *Agrobacterium* strain of step (1) such that the polynucleotide encoding the drought-resistance protein is introduced into the plant cell, organ or tissue;
(4) optionally, selecting a plant cell;
(5) growing the plant cell, organ or tissue into a plant.

7. The method according to claim 1, wherein the plant is selected from the group consisting of dicotyledon, monocotyledon and gymnosperm.

8. The method according to claim 1, wherein the plant is selected from the group consisting of wheat, barley, rye, rice, corn, sorghum, beet, apple, pear, plum, peach, apricot, cherry, strawberry, *Rubus* swinhoei Hance, blackberry, bean, lentil, pea, soy, rape, mustard, opium poppy, *olea europea, helianthus*, coconut, plant producing castor oil, cacao, peanut, calabash, cucumber, watermelon, cotton, flax, *cannabis*, jute, citrus, lemon, grapefruit, spinach, lettuce, asparagus, cabbage, *Brassica campestris* L. ssp. *Pekinensis, Brassica campestris* L. ssp. *chinensis*, carrot, onion, murphy, tomato, green pepper, avocado, *cassia*, camphor, tobacco, nut, coffee, aubergine, sugar cane, tea, pepper, grapevine, nettle grass, banana, natural rubber tree and ornamental plant.

9. The method according to claim 1, wherein the drought-resistance protein has the amino acid sequence of SEQ ID NO:4.

10. The method according to claim 1, wherein the drought-resistance protein has at least 95% sequence identity to the amino acid sequence of SEQ ID NO:4.

* * * * *